Figure 1:
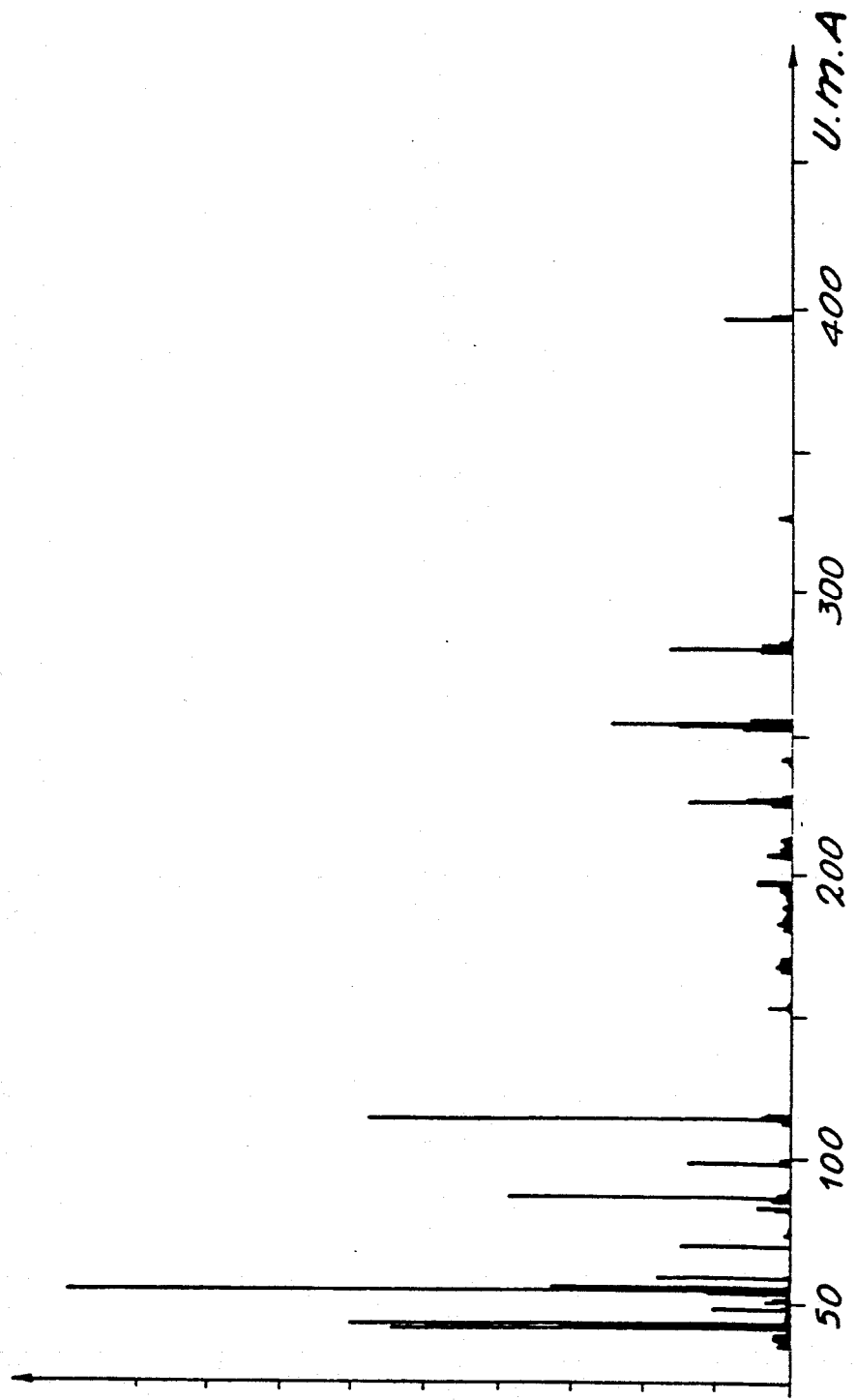

United States Patent [19]

Mahuzier et al.

[11] Patent Number: 5,082,942
[45] Date of Patent: Jan. 21, 1992

[54] NOVEL DERIVATIVES OF TETRAHYDRO-2,3,6,7,1H,5H,11H-(1)BENZOPYRANO(6,7,8,IJ)QUINOLIZINONE-11 USABLE AS MARKERS OF ORGANIC COMPOUNDS FOR THE DETECTION OF SAID COMPOUNDS BY CHEMILUMINESCENCE OR FLUORESCENCE

[75] Inventors: Georges Mahuzier; Joseph Chalom, both of Paris; Robert Farinotti, Champigny sur Marne; Michel Tod, Paris, all of France

[73] Assignee: Laboratories Eurobio, Paris, France

[21] Appl. No.: 613,644
[22] PCT Filed: Jun. 2, 1989
[86] PCT No.: PCT/FR89/00277
§ 371 Date: Jan. 31, 1991
§ 102(e) Date: Jan. 31, 1991
[87] PCT Pub. No.: WO89/12052
PCT Pub. Date: Dec. 14, 1989

[30] Foreign Application Priority Data

Jun. 2, 1988 [FR] France .................. 88 07355

[51] Int. Cl.⁵ .......................... C07D 491/147
[52] U.S. Cl. .......................... 546/66; 546/62; 546/72
[58] Field of Search .................. 546/66, 72

[56] References Cited

U.S. PATENT DOCUMENTS 4,005,092  1/1977  Reynolds ............... 546/66
4,558,130 12/1985  Buckler et al. ......... 546/66
4,736,832  4/1988  Fox et al. ............. 546/66

FOREIGN PATENT DOCUMENTS 3322946  1/1985  Fed. Rep. of Germany ........ 546/66

OTHER PUBLICATIONS

Makuzier, G. et al. CA 113:23889n (1990).
Tod, M. et al., CA 112:151038a (1990).
Optics Communications, vol. 15, No. 3, Drexhage et al., "Water-Soluble Coumarin Dyes for Flashlamp-Pumped Dye Lasters", pp. 399–403.
Journal of Chromatography, vol. 225, 1981, Elsevier Scientific Publishing Co., Cisse et al. "Dosage de l'Acide Dipropylacetique dans le Plasma par Chromatographie en Phase Liquide et Detection Spectrofluorimetrique", pp. 509–515.

Primary Examiner—Allen J. Robinson
Assistant Examiner—Susan P. Treanor
Attorney, Agent, or Firm—Pearne, Gordon, McCoy & Granger

[57] ABSTRACT

The invention concerns new derivatives of tetrahydro-2,3,6,7,1H,5H,11H-(1)benzopyrano(6,7,8, ij)quinolizinone in accordance with formula:

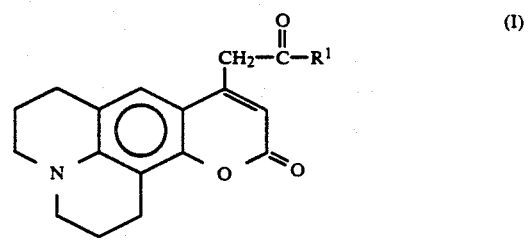

in which $R^1$ represents a radical having formula:

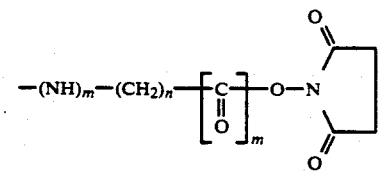

wherein m is equal to 0 or 1, and n is equal to 0 or is a whole number from 1 to 12, provided that n is equal to 0 when m is 0, or the radical having the formula:

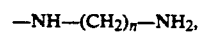

$-NH-(CH_2)_n-NH_2$, in which n has the above meaning.

Said derivatives can be used as markers for organic compounds, in order to detect them by chemiluminescence or fluorescence.

16 Claims, 8 Drawing Sheets

U.m.A

NOVEL DERIVATIVES OF TETRAHYDRO-2,3,6,7,1H,5H,11H-(1)BENZOPYRANO(6,7,8,IJ)QUINOLIZINONE-11 USABLE AS MARKERS OF ORGANIC COMPOUNDS FOR THE DETECTION OF SAID COMPOUNDS BY CHEMILUMINESCENCE OR FLUORESCENCE

The invention relates to novel markers usable for marking organic compounds having —NH—, —NH$_2$, —CHO, —COOH or —CO—groups, with a view to the detection of these compounds by chemiluminescence or fluorescence in determination processes such as liquid chromatography.

It is known that the determination by liquid chromatography of amines, aldehydes, ketones or acids not having spectral properties requires, in order to achieve a high sensitivity, the transformation of these compounds with the aid of marking reagents in order to give them absorption, fluorescence or chemiluminescence properties.

The use of markers of this type for the detection of carboxylic derivatives or amines is in particular described by H. Cisse, R. Farinotti, S. Kirkiacharian and A. Dauphin in Journal of Chromatography, 225, 1981, pp.509–515; by M. Tsitini Tsamis, A. M. Mange, R. Farinotti and G. Mahuzier in Journal of Chromatography, 277, 1983, pp.61–69; by N. Kubab, R. Farinotti and G. Mahuzier in Analysis, 1986, v.14, no.3, pp.125–130; and by D. Amir and E. Haas in Int. J. Peptide Protein Res., 26, 1986, pp.7–17.

In liquid chromatography determination processes, in particular chemiluminescent markers are sought, because analysis by chemiluminescence is subject to a large amount of development and makes it possible to improve the sensitivity of the determination. Thus, chemiluminescence methods make it possible to obtain a detection limit of approximately 1 femtomole, whereas in spectrofluorimetric methods, the detection limit currently reached is a few hundred femtomoles.

A detection method of chemiluminescence in liquid chromatography is in particular described by M. Tod, R. Farinotti and G. Mahuzier in Analysis, 1986, v.14, no.6, pp.271–280.

The presently used chemiluminescent markers such as orthophthalaldehyde, fluorescamine and anthracene and dansylated derivatives suffer from certain disadvantages. Thus, orthophthalaldehyde and fluorescamine are not very sensitive. Anthrazcene derivatives are inhibited by dissolved oxygen and dansylated derivatives are inhibited by certain excitation reaction products. Moreover, certain chemiluminescent markers have a by no means negligible toxicity, which is in particular the case with anthracene and dansylated derivatives.

As a result of recent research, it has been found that coumarin nuclei were of a certain interest, because they have an equivalent sensitivity to the highest performance products, which have neither toxicity, nor sensitivity with respect to the conventional inhibitors, such as dissolved oxygen, halide and nitro derivatives. In addition, they are easy to use under varied excitation and chromatography conditions.

The present invention specifically relates to novel doumarin derivatives in the form of derivatives of tetrahydro-2,3,6,7,1H,5H,11H-(1)benzopyrano(6,7,8 ij)-quanolizinone-11 complying with the formula:

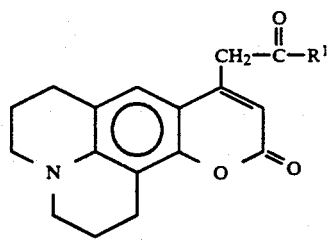

in which R$^1$ represents the radical of formula:

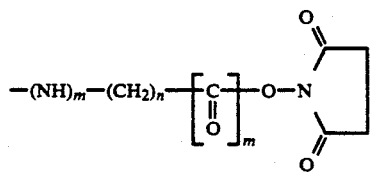

in which m is equal to 0 or 1 and n is equal to 0 or an integer between 1 and 12, provided that n is equal to 0 when m is equal to 0, or the radical of formula:

—NH—(CH$_2$)$_n$—NH$_2$ in which n has the meaning given hereinbefore.

In these novel derivatives, the use of the coumar in nucleus of formula:

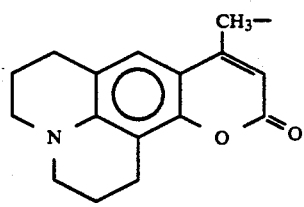

makes it possible to obtain improved fluorescence and chemiluminescence properties. Moreover, the choice of an appropriate —CO—R$^1$ group fixed to this coumarin nucleus makes it possible to obtain markers which can be used for a large number of organic compounds.

Thus, the novel derivatives according to the invention have the advantage of a good sensitivity, the capacity of being used as markers for different compounds, of being usable in the normal or reverse phase, of not being inhibited by the conventional quenchers such as dissolved oxygen, halides and nitrates, of having under no toxicity and of rapidly reacting with the compounds to be marked under relatively gentle conditions.

According to a first embodiment of the invention, the radical R$^1$ represents the radical:

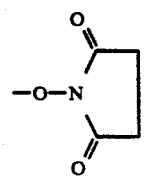

This derivative is tetrahydro-2,3,6,7,1H,5H, 11H(1)-benzo-pyrano(6,7,8-ij) succinimidoxycarbonylmethyl-9 quinolizinone-11, hereinafter called luminarine-1 and complying with the formula:

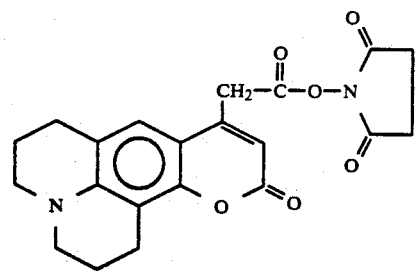

(II)

This derivative is of great interest because it can react with compounds having primary or secondary amine functions, and the derivative formed after said reaction can undergo liquid chromatography and can be detected by absorptiometry, by fluorimetry and by chemiluminescence. In the latter case, which corresponds to the maximum sensitivity, the excitation reaction can use an oxalic ester and hydrogen peroxide, which form peroxyoxalate, a high energy reaction intermediate, which transfers its energy to the derivative of formula (II), which is deexcited whilst emitting light. This determination by chemiluminescence can be applied to molecules having a biochemical or pharacological interest with a view to studies of the metabolism or of a pharmacokinetic nature, particularly determinations of amino acids, biogenic amines of the histamine type, neuromediators of the catecholamine type, hormonal polypeptides and metabolites of phenothiazines, imipraminics, etc. This derivative of formula (II) consequently has numerous uses.

According to a second embodiment of the invention, $R^1$ represents the radical of formula:

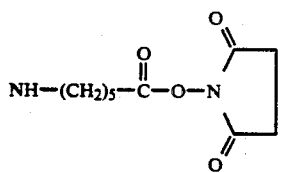

In this case, the coumarin derivative complies with the formula:

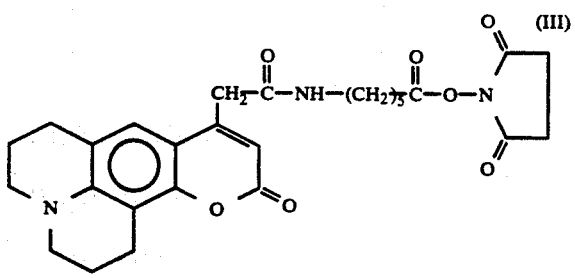

(III)

This derivative, hereinafter called luminarine-2, can react in the same way as luminarine-1 with compounds having primary or secondary amine functions. The derivative formed can undergo chromatography and be detected by absorptiometry, fluorimetry or chemiluminescence. Thus, it is possible to use luminarine-2 for the determination of biogenic amines of the histamine and hydroxyethyl histamine type in an aqueous medium.

According to a third embodiment of the invention, $R^1$ represents the radical of formula —NH—NH$_2$. This coumarin derivative, hereinafter called luminarine-3, complies with the formula:

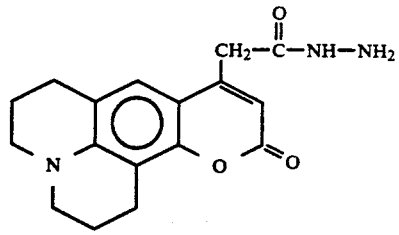

(IV)

It can react with ketones and aldehydes and can consequently be used for the determination of steroids in a polar medium, e.g. in a hydroalcoholic medium.

According to a fourth embodiment of the invention, the radical $R^1$ complies with the formula:

—NH—(CH$_2$)$_4$—NH$_2$

The corresponding coumarin derivative, hereinafter called luminarine-4, complies with the formula:

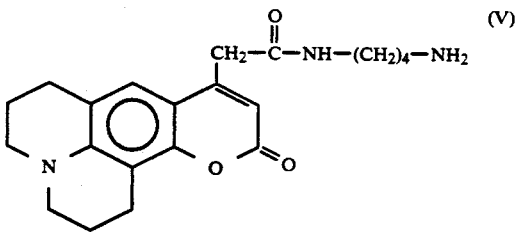

(V)

This derivative can react with carboxylic acids (or the corresponding anhydrides) and is consequently suitable for the detection of acids in a polar medium, e.g. an alcoholic medium. For example, it can be used for methyl imidazolacetic acid determination.

The novel coumarin derivatives of the invention can be prepared by conventional processes.

Thus, it is possible to prepare the derivative of formula (II) by a process having the following successive stages: 1) reacting 8-hydroxyjulolidine of formula:

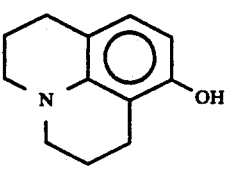

(VI)

with an oxo-3-glutaric acid alkyl ester of formula:

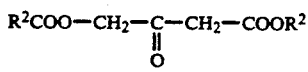

$R^2COO—CH_2—C—CH_2—COOR^2$
$\phantom{R^2COO—CH_2—}\overset{\|}{O}$ in which $R^2$ is an alkyl radical for forming a compound of formula:

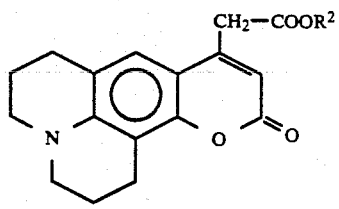 (VII)

2) hydrolyzing the alkyl ester of formula (VII) obtained hereinbefore to obtain the acid of formula:

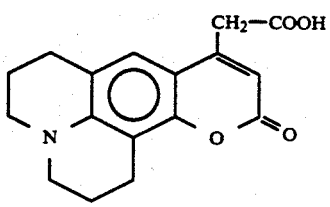 (VIII)

3) reacting the acid of formula (VIII) obtained in this way with dihydroxysuccinimide oxalate of formula:

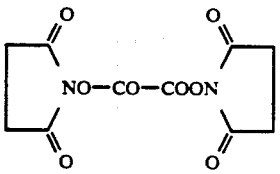 (IX)

In this process, the first stage can be carried out by refluxing, accompanied by stirring, the 8-hydroxyjulolidine with the oxo-3-glutaric acid alkyl ester, in the presence of anhydrous zinc chloride and in alcoholic solution. The compound of formula (VII) obtained can be separated by extraction by means of an organic solvent such as ethyl acetate.

In the second stage of the process, it is possible to carry out the hydrolysis of the alkyl ester of formula (VII) by an aqueous soda solution in an alcoholic solution constituted e.g. by methanol.

The third stage of the process can e.g. be carried out by reacting the acid of formula (VIII) with dihydroxysuccinimide oxalate in an anhydrous organic solvent, in the presence of anhydrous triethyl amine. Under these conditions, it is possible to obtain the coumarin derivative of formula (II) with a high degree of purity, namely approximately 90%.

The coumarin derivatives in accordance with formula:

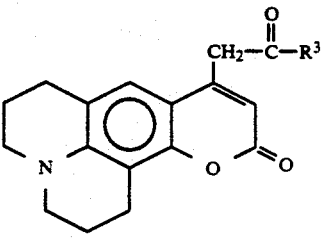 (X)

in which $R^3$ represents the radical of formula:

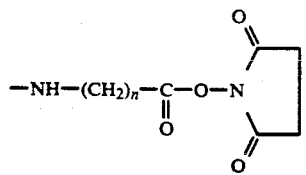

in which n is an integer between 1 and 12 can be prepared by a process comprising the following successive stages:

a) reacting the compound of formula:

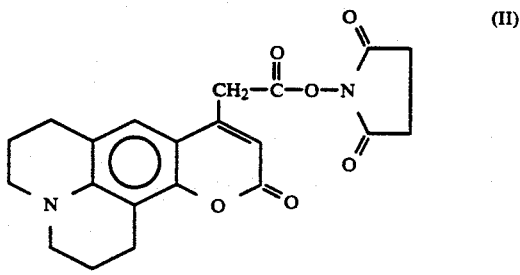 (II)

with an alkyl aminocarboxylate of formula:

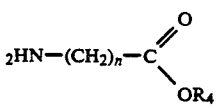

in which $R^4$ is an alkyl radical with 1 to 4 carbon atoms and n has the meaning given hereinbefore in order to form a compound of formula:

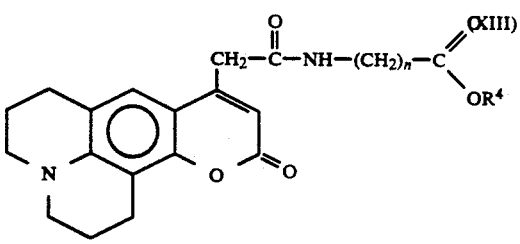 (XIII)

b) hydrolyzing the ester of formula (XIII) obtained to form the acid of formula:

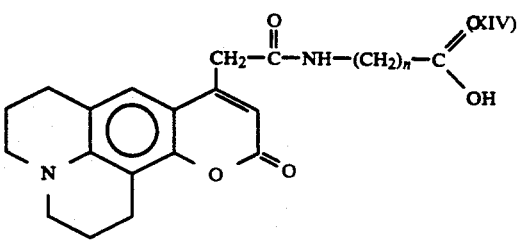 (XIV)

c) reacting the acid of formula (XIV) obtained in this way with 1) dihydroxysuccinimide carbonate of formula:

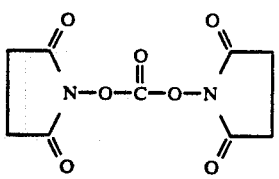 (XV)

2) dihydroxysuccinimide oxalate or 3) hydroxysuccinimide in the presence of dicyclohexyl carbodiimide.

For example, when n is equal to 5, it is possible to react the luminarine-1 of formula (II) with methyl-6-aminohexanoate and then hydrolyze the ester obtained into acid and transform the acid into hydroxysuccinimide ester by the action of hydroxysuccinimide oxalate or carbonate or by hydroxysuccinimide action in the presence of dicyclohexyl carbodiimide.

The coumar in derivatives of formula (X) in which $R^3$ is the radical of formula $-NH-(CH_2)_n-NH_2$ in which n is an integer from 1 to 12 can be prepared by a process consisting of reacting the compound of formula:

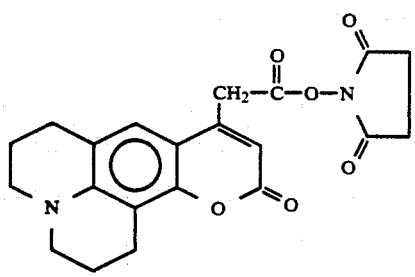 (II)

with a diaminoalkane of formula:

$$2HN-(CH_2)_n-NH_2$$

in which n has the meaning given hereinbefore.

For example, when n is equal to 4, it is possible to react the methyl ester of formula (VII) with 1,4-butane diamine.

The coumar in derivative complying with formula:

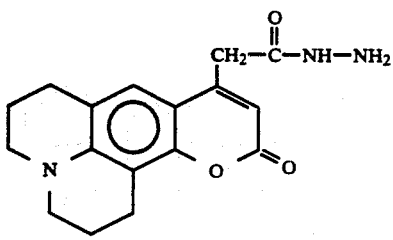 (IV)

can be prepared by the process comprising the following successive stages:

1) reacting the 8-hydroxyjulolidine of formula:

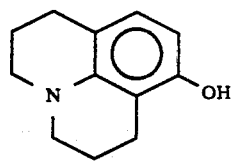 (VI)

with an oxo-3-glutaric acid alkyl ester of formula:

$$R^2COO-CH_2-\underset{\underset{O}{\|}}{C}-CH_2-COOR^2$$

in which $R^2$ is an alkyl radical to form a compound of formula:

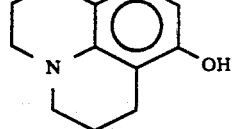 (VII)

2) reacting the alkyl ester of formula (VII) obtained in this way with hydrazine hydrate $2HN-NH_2, H_2O$.

The ester of formula (VII) can in particular be methyl ester.

In the process described hereinbefore for the preparation of coumarin derivatives of formula (II) or (X), the oxo-3-glutaric acid alkyl ester is an ester in which the alkyl group preferably has 1 to 2 carbon atoms. For example, it is possible to use ethyl ester.

The starting products used in these various preparation methods for the coumarin derivatives according to the invention are commercially available products or can be prepared by conventional processes starting from commercially available products.

As stated hereinbefore, the coumarim in derivatives according to the invention can react with different organic compounds, e.g. amines in the case of luminarine-1 and luminarine-2, aldehydes and ketones in the case of luminarine-3 and carboxylic acids in the case of luminarine-4.

In addition, these coumarin derivatives can be used as markers for organic compounds having primary or secondary amine, aldehyde, ketone or carboxylic acid functions and can be used for the detection of these compounds in liquid chromatography determination methods. Detection can take place by absorptiometry, fluorimetry or chemiluminescence using conventional procedures of the type described by M. Tsitini Tsamis et al in Journal of Chromatography, 277, 1983, pp.61-69; D. Amir and E. Haas in Int. J. Peptide Protein Res. 26, 1986, pp.7-17, H. Cisse et al in Journal of Chromatography, 225, 1981, pp.509-515; and M. Tod et al in Analysis, 1986, v.14, no.6, pp.271-280.

In addition, the invention also relates to a process for detecting a compound having a primary or secondary amine function by liquid chromatography, which consists of reacting the compound to be detected with a derivative according to formula:

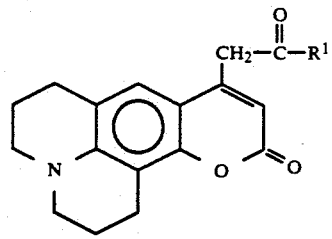
(I)

in which $R^1$ represents the radical of formula:

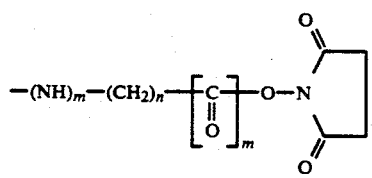

in which m=0 or 1 and n=0 or is an integer from 1 to 12, provided that n=0 when m=0, in order to form a derivative of the compound to be detected, followed by a separation of said derivative by liquid chromatography and the detection of said derivative by absorptiometry, fluorimetry or chemiluminescence.

Preferably detection takes place by chemiluminescence using an oxalic ester and hydrogen peroxide.

For example, the oxide ester can be bis-(2,4,6-trichlorophenyl)-oxalate (TCPO) or bis-(2,4-dinitrophenyl)-oxalate (DNPO).

The invention is described in greater detail hereinafter relative to non-limitative examples and with reference to the attached drawings, wherein show:

FIG. 1—The mass spectrum of luminarine-1.

Figure 2:
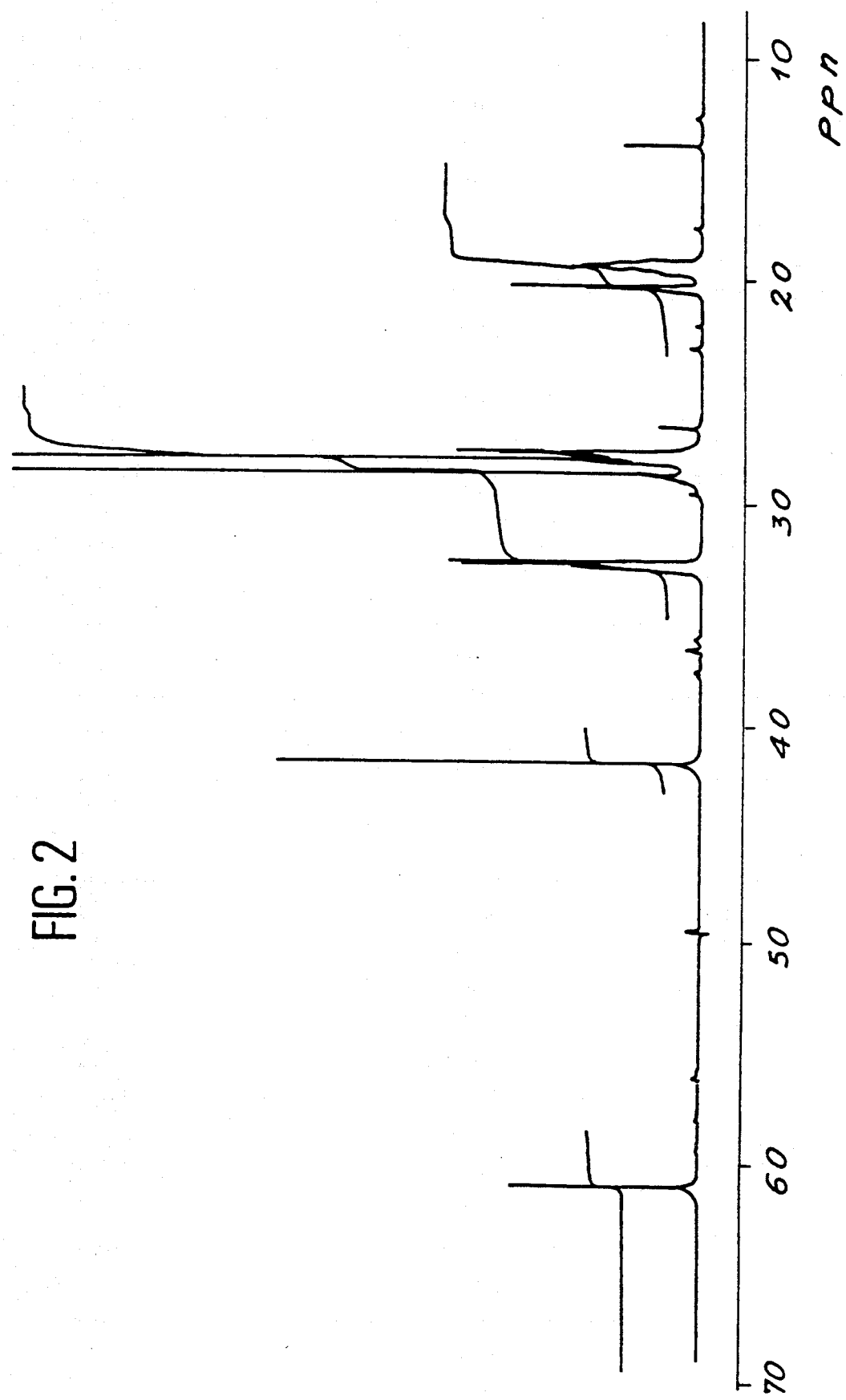

FIG. 2—The nuclear magnetic resonance spectrum of the proton of luminarine-1.

Figure 3:
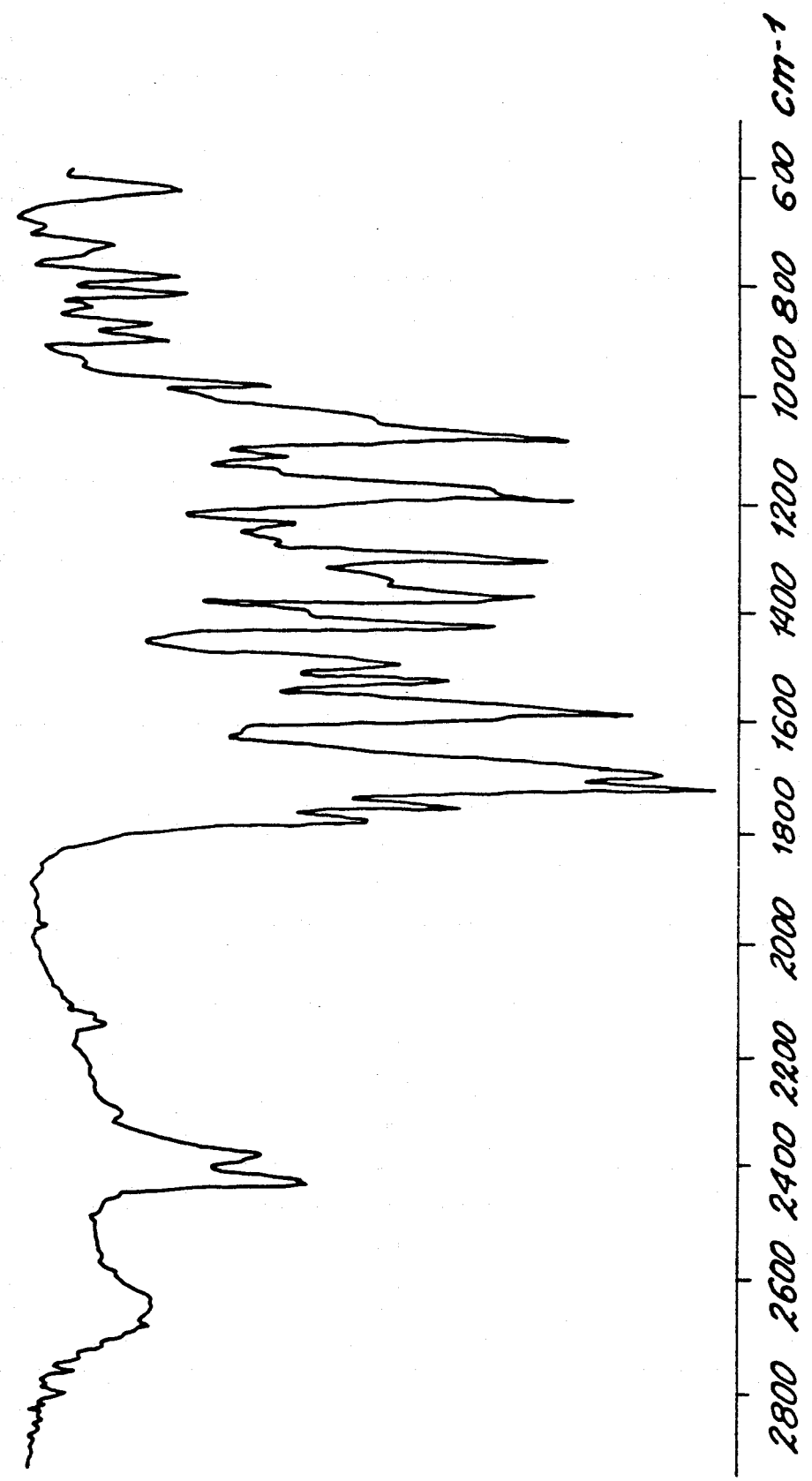

FIG. 3—The infrared spectrum of luminarin-1.

Figure 4:
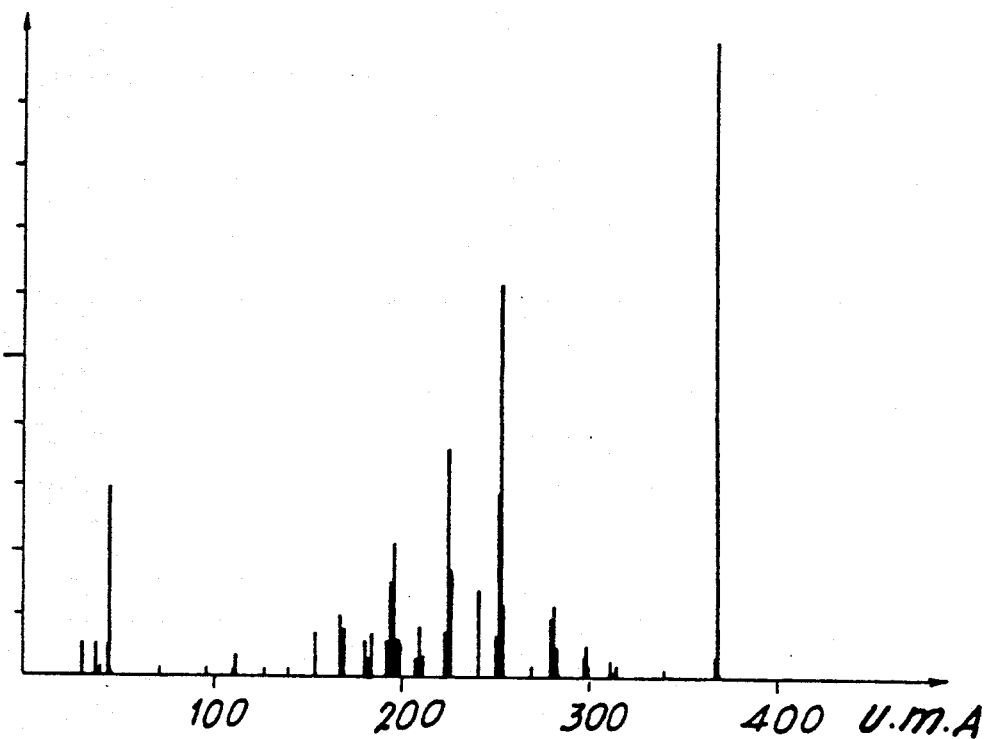

FIG. 4—The mass spectrum of the derivative obtained by reacting pentylamine with luminarine-1.

Figure 5:
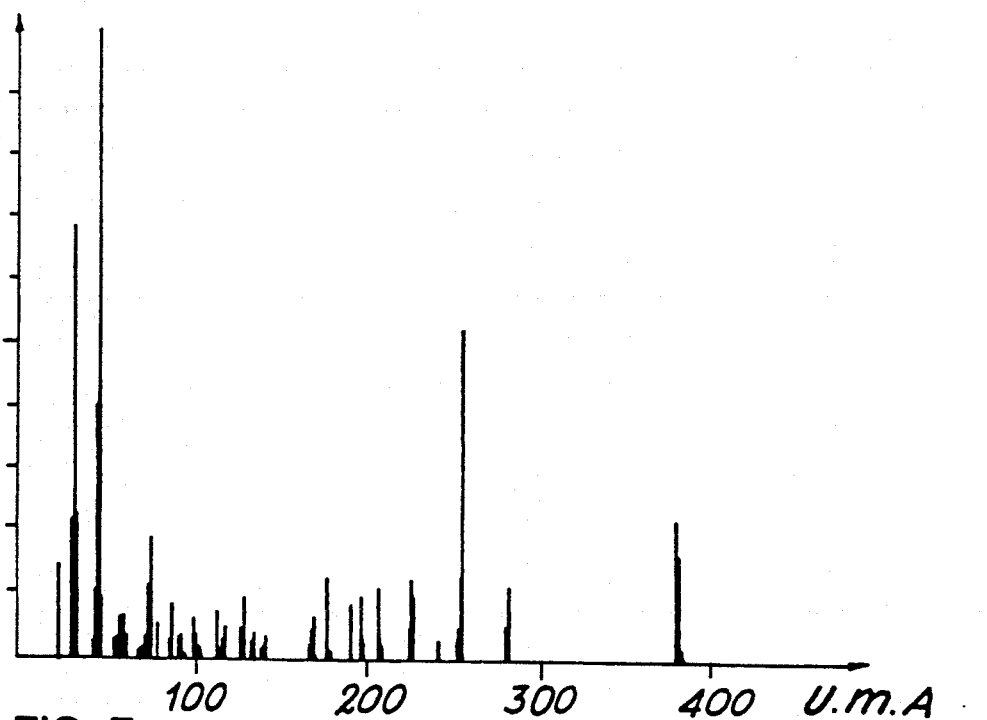

FIG. 5—The mass spectrum of the derivative obtained by reacting dipropylamine with luminarine-1.

Figure 6:
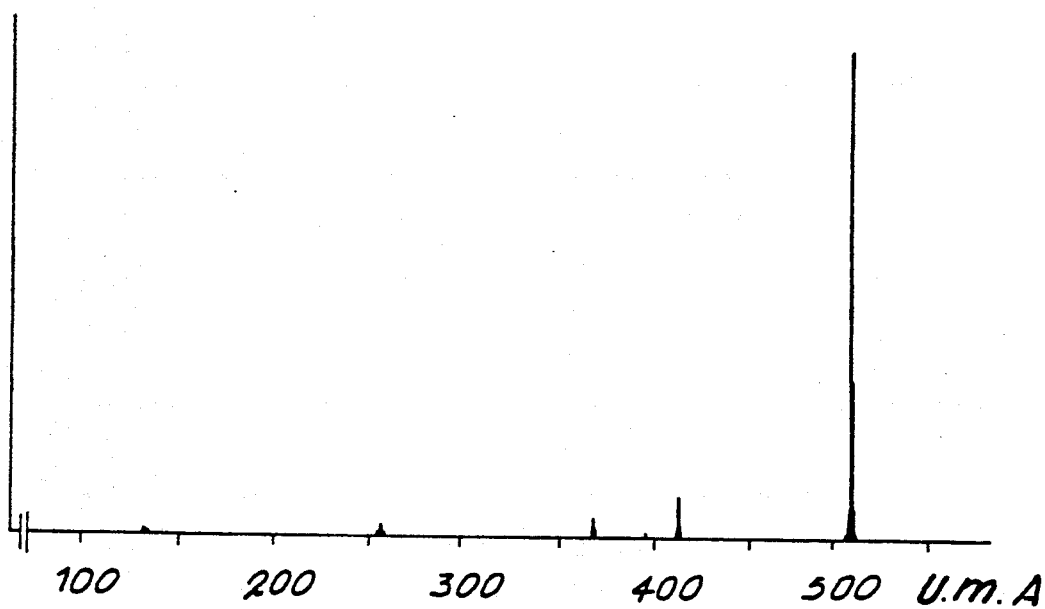

FIG. 6—The mass spectrum of luminarine-2.

Figure 7:
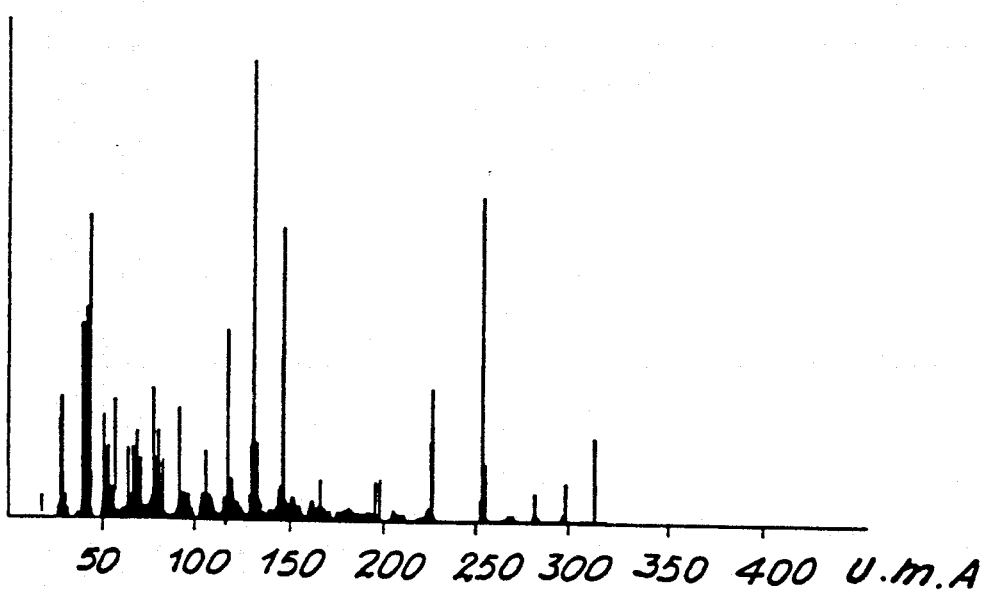

FIG. 7—The mass spectrum of luminarine-3.

Figure 8:
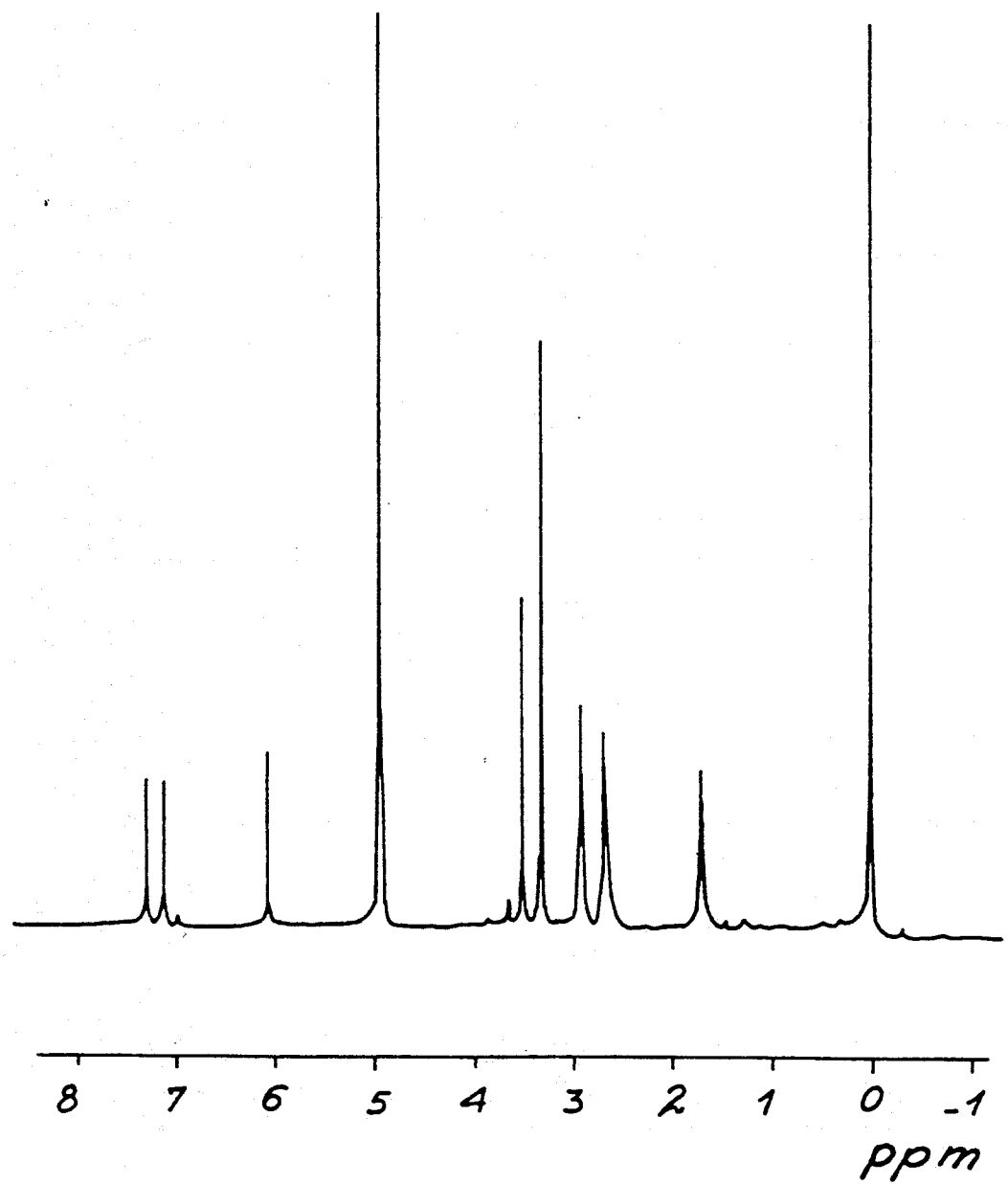

FIG. 8—The nuclear magnetic resonance spectrum of the proton of luminarine-3.

Figure 9:
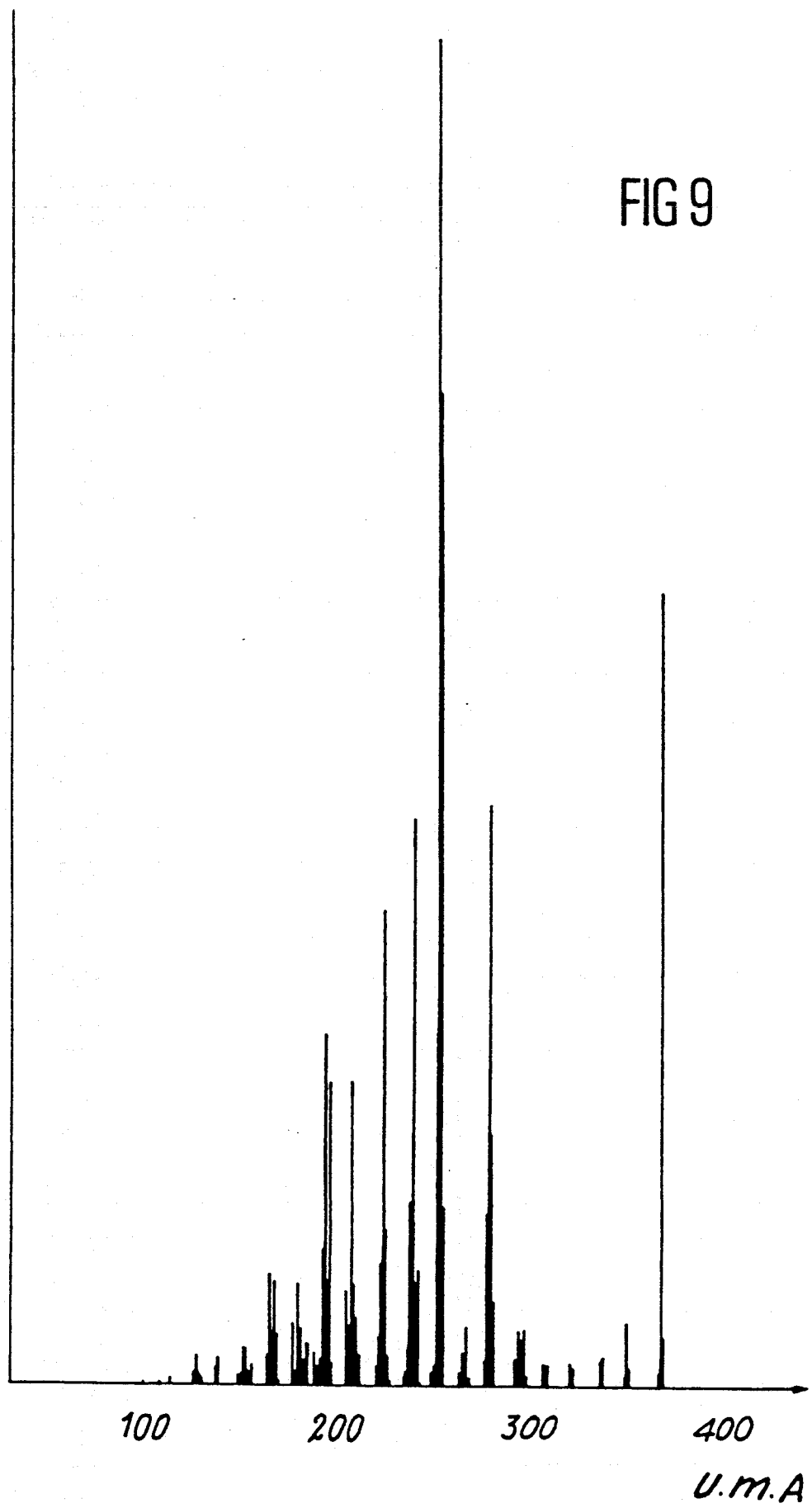

FIG. 9—The mass spectrum of luminarine-4.

Figure 10:
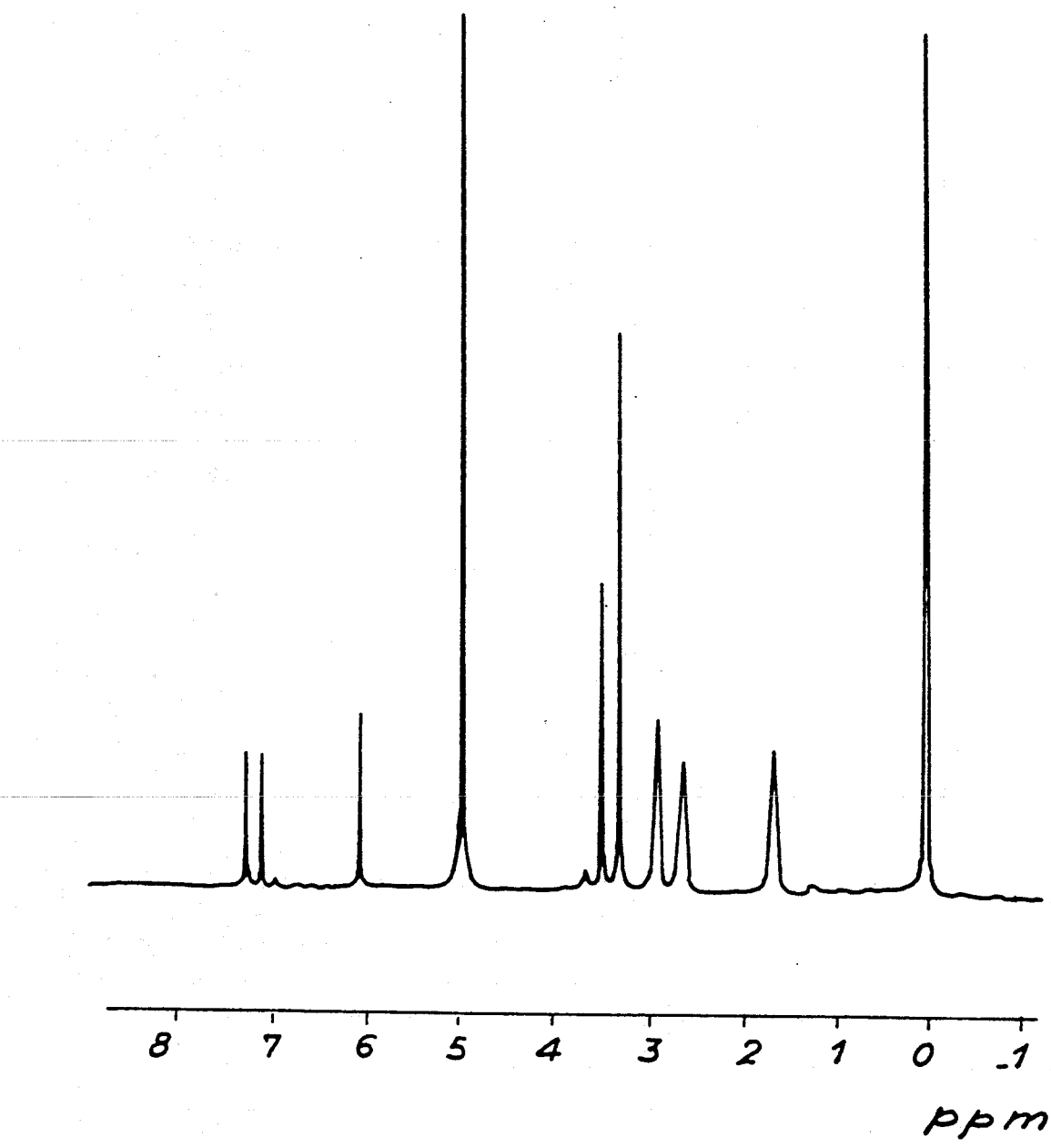

FIG. 10—The nuclear magnetic resonance spectrum of the proton of luminarine-4.

EXAMPLE 1

Synthesis of luminarine-1 In Accordance With Formula

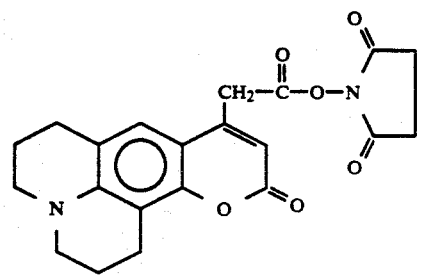
(II)

a) Preparation of the Compound of Formula (VII) With $R^2$ Representing the Ethyl Radical The reaction performed here corresponds to the following reaction diagram:

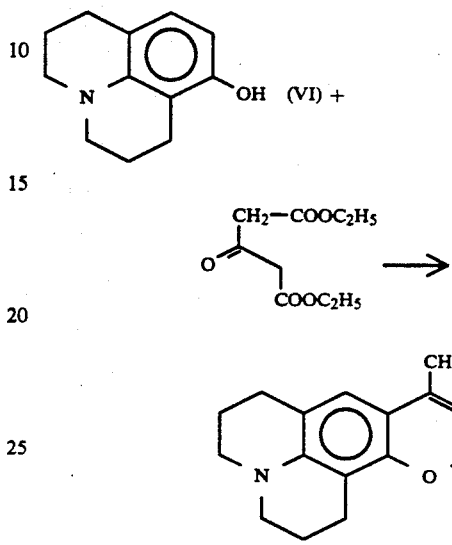

2.12 g of 8-hydroxyjulolidine, 2.22 g of oxo-3-glutaric acid ethyl ester, 1.71 g of anhydrous zinc chloride and 6 ml of anhydrous ethanol are introduced into a container, followed by refluxing for 24h, accompanied by stirring and protected from moisture. After cooling, the solution is introduced into 200 ml of water, followed by extraction by 200 ml and then 100 ml of ethyl acetate. The organic phase is washed with water, dried on magnesium sulphate and concentrated to dryness. This is followed by recrystallization in 5 parts of ethyl acetate. This gives the ethyl ester of formula (VII) with a 56% yield.

b) Hydrolysis of the Ethyl Ester of Formula (VII) Obtained Hereinbefore 2 g of the previously obtained ethyl ester with 42 ml of an aqueous 1.2 wt./vol. aqueous NaOH solution and 40 ml of methanol are introduced into a container, followed by heating to 45° C. for 1 hour. After cooling, the reaction medium is extracted by 50 ml and then 40 ml of chloroform. After degassing, the aqueous phase is acidified with 16 ml of 3N hydrochloric acid. Stirring of the reaction mixture is then maintained for 15 min. The pH is then adjusted to 6.5 with 13 ml of 2.5N soda. The precipitate formed is then filtered, rinsed with water and dried. This gives the acid of formula (VIII) with a 90% yield.

c) Obtaining luminarine-1

In this third stage, the acid of formula (VIII) obtained in the preceding stage is reacted with dihydrosuccinimide oxalate according to the following reaction diagram:

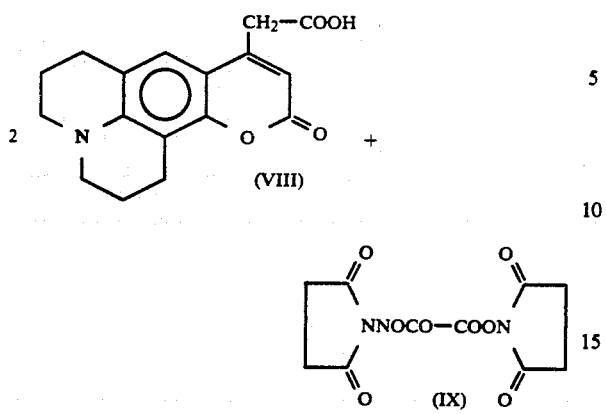

(VIII)

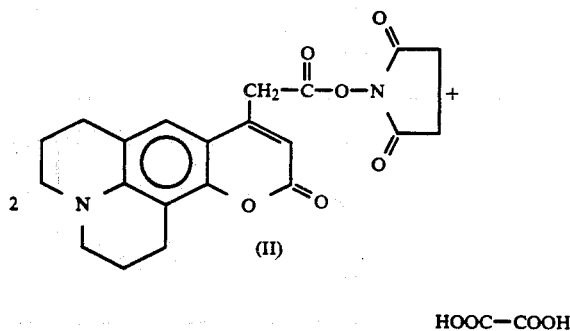

(IX)

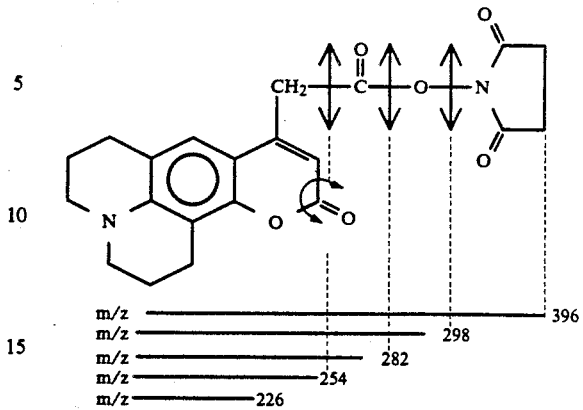

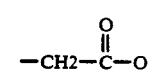

(II)

1.5 g of the acid of the formula (VIII), 2.13 g of dihydroxysuccinimide oxalate, 0.51 g of anhydrous triethylamine and 220 ml of anhydrous acetonitrile are introduced into a container. The mixture is stirred, protected from moisture for 1 hour and at ambient temperature and then for 1 hour at 35° to 40° C. Slight insoluble are filtered, followed by vacuum concentration and purification by silica gel chromatography using as the elution solvent a mixture of dichloromethane and tetrahydrofuran (THF) with a volume ratio of 1:1. Fractions 11 to 14 are concentrated, which gives luminarine-1 with a 21% yield.

The structure of luminarine-1 is confirmed by the following methods:

1) Determination of the Empirical Formula

| | $C_{21}H_{20}O_6N_2$ | | | |
|---|---|---|---|---|
| | C | H | N | O |
| Calculated | 0.64 | 0.051 | 0.071 | 0.24 |
| Found | 0.635 | 0.051 | 0.070 | 0.24 |

2) Electron Impact Mass Spectrometry at 70 eV With Direct Introduction

The spectrum obtained is shown in FIG. 1 and it is possible to see the molecular peak at 396 and the main fragments at 298, 282, 254 and 226, which corresponds to the following structure:

3) Nuclear Magnetic Resonance (NMR) Spectrometry

The NMR spectrum of the proton of luminarine-1 in deuterated acetone is shown in FIG. 2 and corresponds to the following results:

| Displacement (ppm) | Nature | Height | Origin |
|---|---|---|---|
| 1.94 | Multiplet | 4 H | CH2—CH2—N—CH2—CH2 |
| 2.78 | Sextuplet | 4 H | CH2—N—CH2 |
| 2.88 | Singlet | 4 H | Succinimide |
| 3.29 | Multiplet | 4 H | CH2 in 6 and 8 |
| 4.18 | Singlet | 2 H | $-CH_2-\overset{\overset{O}{\|}}{C}-O$ |
| 6.11 | Singlet | 1 H | —C—H in 3 |
| 7.13 | Singlet | 1 H | H in 5 |

4) Infrared Spectrometry

The infrared spectrum of luminarine-1 in KBr pellet is shown in FIG. 3 and corresponds to the following results:

| Wave Number cm$^{-1}$ | Transmission % | Origin |
|---|---|---|
| 2940 | 53 | Asymmetric value CH3 |
| 2840 | 58 | Symmetric value CH3 |
| 1800 | 45 | — |
| 1770 | 34 | C=O value of succinimide |
| 1730 | 3 | C=O value of pyrone |
| 1700 | 8 | C=O value of ester |
| 1590 | 11 | |
| 1550 | 35 | Aromatic value C=C |
| 1510 | 39 | |
| 1420 | 32 | — |
| 1370 | 24 | — |
| 1310 | 23 | Aromatic value C—N |
| 1260 | 54 | Pyrone value C—O—C |
| 1200 | 20 | — |
| 1090 | 20 | — |
| 990, 920 | 72 | Aromatic Def C—H |
| 840, 800, 655 | 68, 69, 68 | — |

The purity of luminarine-1 is also determined by high pressure liquid chromatography and fluorimetric detection. The purity is 90%. The main impurity is constituted by the acid of formula (VIII). Gas chromatographic and mass spectrometric analysis reveals, in addition to the acid of formula (VIII), small amounts of other impurities constituted by the ethyl ester of formula (VII) and the decarboxylation product of the acid of formula (VII).

Luminarine-1 is a crystalline yellow powder which can be kept in a brown bottle protected from light and which can be dissolved in tetrahydrofuran, acetone or methanol, its solubility in these organic solvents being approximately 1 g/l.

The stability of a $2.10^{-3}$ mole/l solution of luminarine-1 in tetrahydrofuran was studied by high pressure liquid chromatography and fluorimetric detection. It was found that the product in solution deteriorates significantly in a few hours at ambient temperature by hydrolysis, accompanied by the formation of the acid of formula (VIII). However, the frozen solution can be kept for at least two months without any apparent deterioration.

EXAMPLE 2

Reaction of luminarine-1 With Pentylamine

This reaction corresponds to the following reaction diagram:

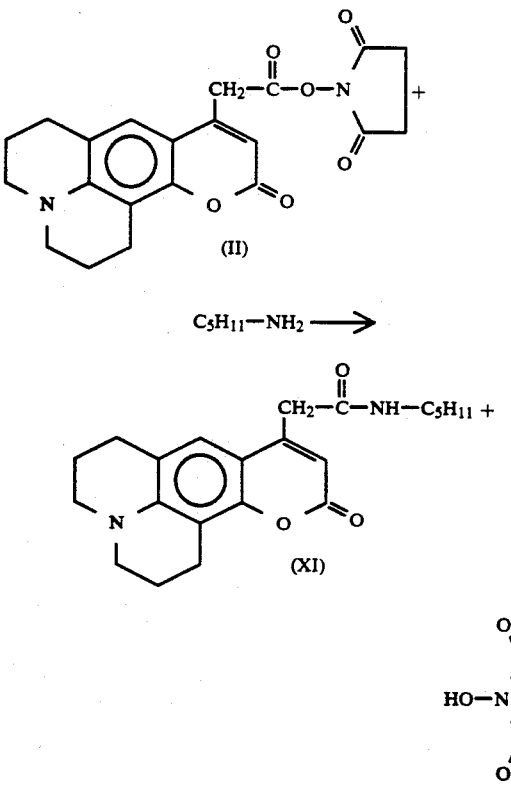

4 g of luminarine-1 are reacted with 0.9 g of pentylamine in 2000 ml of THF at 50° C. for 20 min. This gives the pentylamine derivative of formula (XI) with a 97% yield. The structure of said derivative was confirmed by gas chromatography and mass spectrometry.

FIG. 4 shows the mass spectrum of the pentylamine derivative and the luminarine of formula (XI).

EXAMPLE 3

Reaction of luminarine-1 With Dipropylamine

The reaction is carried out as in example 2 by reacting 4 g of luminarine with 0.9 g of dipropylamine in 2000 ml of THF, at 80° C. and for 30 min, in the presence of pyridine as the catalyst. The product obtained is analyzed by gas chromatography and mass spectrometry.

The mass spectrum is shown in FIG. 5 and confirms the structure corresponding to the following formula:

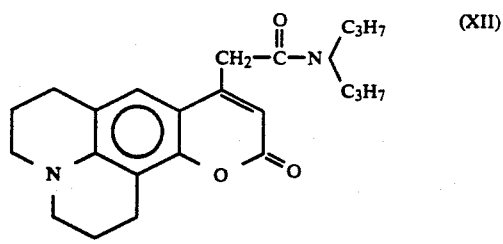

EXAMPLE 4

Use of luminarine-1 for Detecting Pentylamine by Liquid Chromatography

In this example, the derivative of the pentylamine obtained in example 2 undergoes liquid chromatography. The liquid chromatography installation comprises a Chromatem 380 pump, a pulsation damper, a 20 μl Rheodyne injector, a silica column and a Schoeffel FS 970 fluorimetric detector with a Servotrace recorder. This system is completed by a 500 μl Kratos UFR 051 post-column mixer and a Shimadzu column oven, detection being carried out by chemiluminescence.

The mobile liquid phase is a mixture of acetonitrile and water with an acetonitrile/water volume ratio of 70:30. This liquid phase is introduced at a flow rate of 1 ml/min and to it is added pure luminarine-1 or the luminarine-1 derivative and pentylamine. The products obtained are detected by fluorescence at the column exit carrying out excitation at 380 nm and by detecting the emission with a high-pass filter at 470 nm.

Under these conditions luminarine-1 is detected 3.2 min following injection, which corresponds to a k' of 2.2 and the luminarine-1 derivative and pentylamine is detected 3.8 min after the injection corresponding of a k' of 2.8.

In a second experiment, detection takes place of the products at the column exit by chemiluminescence using bis-(2,4,6-trichlorophenyl)-oxalate (TCPO) and $H_2O_2$. In this case, the stationary phase is constituted by a 150×4.6 mm licrosphere octadecyl grafted silica column with an average particle size of 3 μm. The mobile phase is a mixture of acetonitrile and imidazole-nitrate buffer at pH 8 and $10^{-2}$ mole/l, with an acetonitrile/buffer volume ratio of 70:30 and a flow rate of 1 ml/min. The chemiluminescence reaction is performed using a $10^{-2}$ mole/l TCPO solution in methylacetate at a flow rate of 0.25 ml/min and a 0.2 mole/l $H_2O_2$ solution in tetrahydrofuran at a flow rate of 0.25 ml/min. Use is made of the same high-pass filter at 470 nm and a column oven maintained at 30° C.

Under these conditions, the luminarine and pentylamine derivative passes out after 1.4 min, which corresponds to a k' of 3.5.

In a third experiment, detection takes place of products leaving the column by chemiluminescence using DNPO and $H_2O_2$. In this case the solid phase used is a 150×4.6 mm silica column with an average particle size of 5 μm. The mobile liquid phase is a mixture of chloroform, hexane, methylacetate and acetic acid in a volume ratio of 66:17:17:0.1 and a flow rate of 2 ml/min. For the chemiluminescence reaction use is made of a 0.4 mole/l $H_2O_2$ solution in acetonitrile at a flow rate of 0.50 ml/min and a 0.006 mole/l solution of bis-(2,4-dinitrophenyl)-oxalate (DNPO) in methylacetate at a flow rate of 0.17 ml/min. Detection takes place with the high-pass filter at 470 nm.

Under these conditions, the luminarine and pentylamine derivative passes out after 2.4 min, which corresponds to a k' of 3.0.

It is pointed out that the detection limit of the derivative of pentylamine and luminarine in liquid chromatography with fluorimetric detection is 380 fmole and that it is considerably improved with detection by chemiluminescence passing to 2 fmole injected, the response being linear between 2 and 500 fmole injected.

In exemplifed manner, the following table 1 gives the results obtained under the same conditions with other chemiluminescent markers. Table 1 shows that the lowest detection limit is obtained with luminarine-1 in chemiluminescence.

EXAMPLE 5

Synthesis of luminarine-2 of Formula:

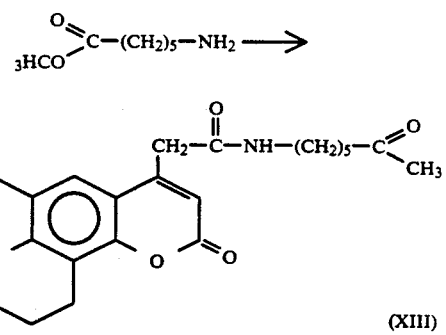

Luminarine-1 (II) is prepared by the action of 11.26 g (0.0377 mole) of acid (VIII), 3.81 g of triethylamine (0.0377 mole) and 10.62 g of di-NN'-succinimidyl carbonate (0.0415 mole) in 560 ml of dry acetonitrile (solution A).

30 g of potassium carbonate are reacted with a solution of 30 g of methyl aminohexanoate hydrochloride (solution B), filtration taking place after 30 hours. Solutions A and B are mixed and stirred for 8 hours. 20 g of ethanol amine are added and stirring takes place for 30 minutes. This is followed by filtration, washing with water, drying the solvent and making dry.

The evaporation residue is purified by silica column chromatography (solvent : $CH_2Cl_2$, $CH_2Cl_2$-THF 85:15, then $CH_2Cl_2$-THF 75-25).

The enriched fractions are recrystallized in ethyl acetate giving a yield of 5.76 g (36%).

b) Hydrolysis of the ethyl ester (XIII) obtained:
On the basis of 1.25 g of ester (XIII), it is possible to obtain 0.76 g of acid (XIV) by operating exactly as in example 1b) (yield =63%).

c) Obtaining luminarine-2 (III), hydroxysuccinimide ester of acid (XIV):

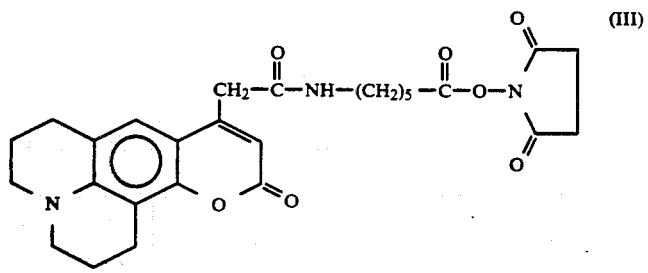

The starting product is luminarine-1 (II) described in example 1 and the following stages are carried out:
a) Action of methyl aminohexanoate on lumarine-1:
The reaction corresponds to the following reaction diagram:

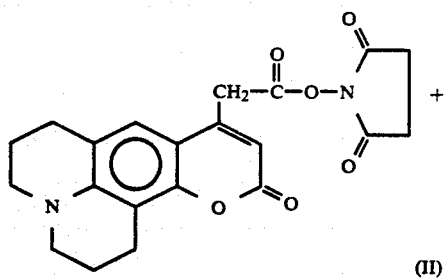

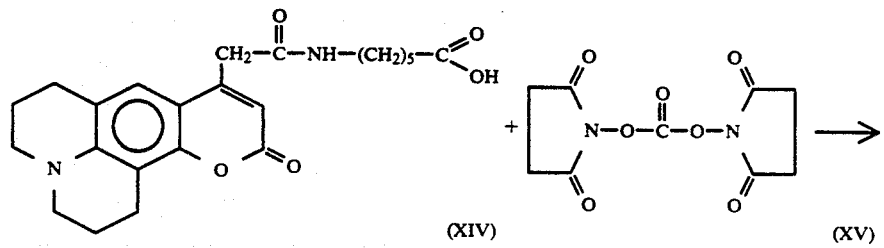

-continued

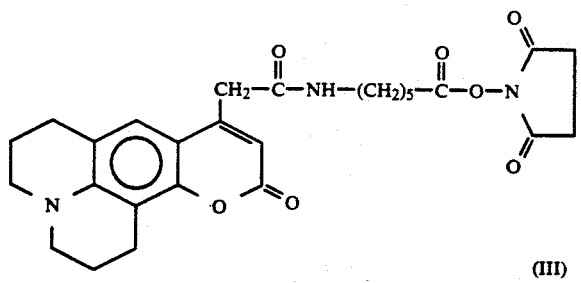

(III)

Reaction takes place for 6 hours of 0.750 g of acid (XIV), 0.912 g of triethylamine, 0.512 g of dihydroxysuccinimide carbonate (XV) in 27 ml of acetonitrile. After filtration and evaporation, purification takes by silica column chromatography (solvent : $CH_2Cl_2$, $CH_2Cl_2$-THF 85:15 then $CH_2Cl_2$-THF 75:25). Yield of pure fractions : 175 mg (19%).

Thus, luminarine-2 is obtained and it is confirmed by mass spectrometry that its structure corresponds to the above formula. The mass spectrum is shown in FIG. 6 and indeed confirms said structure.

EXAMPLE 6

Synthesis of luminarine-3 of formula

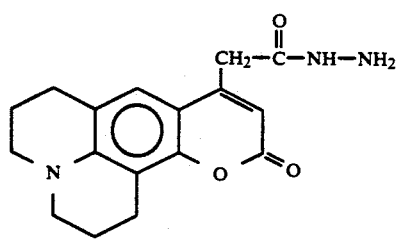

(IV)

The starting product is the ester (VII) ($R_2=CH_3$) described in example 1a), which is reacted with hydrazine hydrate according to the following diagram:

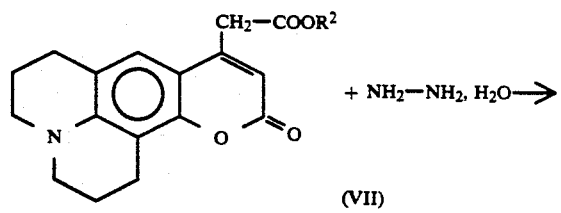

-continued

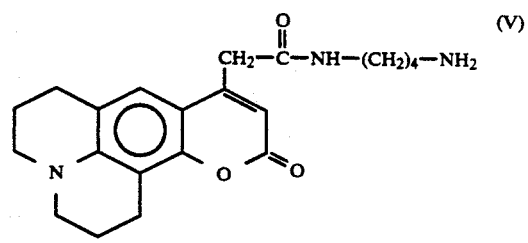

(IV)

Reaction takes place for 4 hours, accompanied by stirring, of 5 g of ester (VII) (15 mmoles) and 8 ml of hydrazine (150 mmoles) in 100 ml of methanol. After 4 hours this is followed by filtering, rinsing with 10 ml of methanol and then with 10 ml of dichloromethane giving a yield of 3.6 g (77%).

By mass spectrometry and NMR it is confirmed that the compound obtained is luminarine-3. The mass spectrum is shown in FIG. 7 and the NMR spectrum in FIG. 8 and confirm that the compound obtained is in accordance with formula IV.

EXAMPLE 7

Synthesis of luminarine-4 of Formula

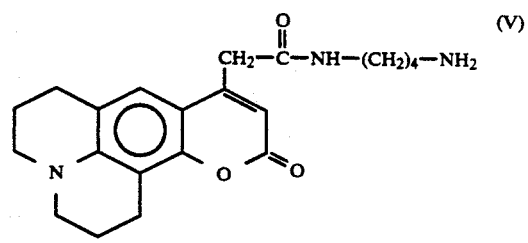

(V)

The same operating procedure as in Example 5, paragraph a) is followed except that the diamine of formula $NH_2$-$(CH_2)_4$-$NH_2$ is used in place of methyl aminiohexanoate.

Purified luminarine-1 (II) is used directly as the starting product and is reacted with 1,4-diaminobutane according to the following reaction diagram;

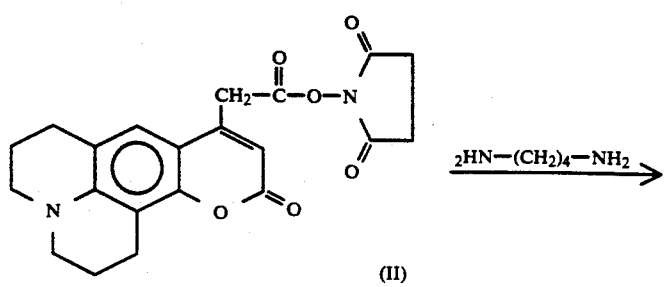

(II)

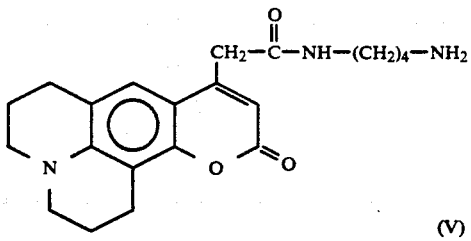

(V)

In a 1 liter round-bottomed flask reaction takes place of 16.5 g of luminarine-1 (II) (41.6 mmole) and 18.3 g of 1,4-diaminobutane ($10^7$ mmoles) in 400 ml of anhydrous THF, accompanied by stirring for 24 hours. A chestnut coloured insoluble is filtered. The mother liquors are concentrated to dryness, the residue is taken up in 100 ml of dichloromethane and extraction takes place by 5×100 ml of water to eliminate the 1,4-diaminobutane excess. The solvent is concentrated to dryness. The residue is stirred in 25 ml of dichloromethane. Yield : 10.6 g (69%).

The structure of the compound obtained is confirmed by mass spectrometry and NMR. The means spectrum is shown in FIG. 7 and the NMR spectrum in FIG. 10 and confirm that the structure of the compound obtained is in accordance with formula (V).

EXAMPLE 8

In order to reveal the improved properties of the luminarines according to the invention, fluorescence, absorbance and chemiluminescence measurements were carried out using as the fluorophore coumarins according to the prior art, namely coumarin-1 ®, dimethylamino-7 methyl-4 coumarin (DEMC) of formula:

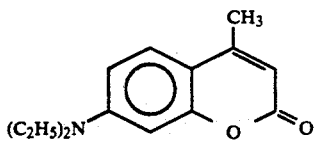

and coumarin-311 ®, dimethylamino-7 methyl-4 coumarin (DMMC) of formula:

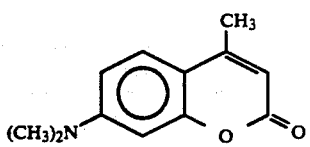

in order to compare them with coumarin-102 ®, tetrahydro-2,3,5,6,7,1H,5H,11H-(1)-benzopyrano (6,7,8-ij) methyl-9 quinolizinone-11(TBMQ), which is the basic nucleus of the derivatives according to the invention of formula:

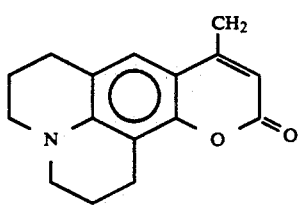

The fluorescence measurements are carried out with a Perkin Elmer LS5 spectrofluorimeter with 2 nm slot widths for two monochromators.

The absorbance measurements are carried out with a Jobin Yvon JY3 spectrophotometer. The chemiluminescence measurements are obtained using a Jobin Yvon JY4 spectrofluorimeter with 10 nm slot widths. The liquid sample cell is a 10×10 mm quartz cup with a capacity of 3 ml and filled with 2 ml of solution, which corresponds to a real solution volume exposed to the photomultiplier of 1.35 ml.

Fluorescence and Absorbance Measurements

These measurements were performed at 20°+2° C. and the quantum efficiencies of fluorescence $R_F$ of coumarins-1, 311 and 102 were determined compared with quinine disulphate, whereof the quantum efficiency of fluorescence is 0.546 using the Parker method described in Analyst, 85, 1960, p.587 with a 2 mg/l quinine disulphate solution in 0.1 N $H_2SO_4$.

For the coumarins, use was made of a solution of acetone and ethylacetate in a volume ratio of 75:25 with a coumarin concentration of $10^{-6}$ mole/l ensuring in each case an absorbance below 0.05.

Chemiluminescence Measurements

In order to determine the quantum efficiencies of chemiluminescence of $R_C$, the intensity was estimated as a function of the time at the emission maximum. When the intensity decrease is relatively low, the emission spectrum is plotted and then the intensity is followed as a function of time until it has dropped to 2% of the maximum intensity.

The other luminescence parameters are measured directly, namely the maximum intensity (Imax), the time for reaching the maximum intensity (Tmax) and the time for reaching half the maximum intensity after the maximum time (T1/2).

The chemiluminescence efficiency $R_C$ is calculated in accordance with the Rauhut method described in J. Am. Chem. Soc., 88, 15, 1966, p.3604.

The excitation efficiency $R_{ex}$ is determined on the basis of the formula:

$$R_C = R_{ex} \times R_F$$

For the chemiluminescence measurements with TCPO, addition takes place of 1 ml of the solution containing $10^{-3}$ mole/l of coumarin, 0.5 ml of a $2.10^{-3}$ mole/l TCPO solution in ethyl acetate, 0.5 ml of a $2.10^{31\ 2}$ mole/l to $H_2O_2$ solution in acetone and 10 μl of an imidazole nitrate buffer, pH 7.5 at 0.1 mole/l . When DNPO is used, to the same solution of coumarin in acetone are added 0.5 ml of a $10^{-3}$ mole/l DNPO solution in ethyl acetate and 0.5 ml of a $10^{-2}$ mole/l $H_2O_2$ solution in acetone.

The fluorescence and absorbance properties of these coumarins are given in table 2 and the chemiluminescence results are given in table 3. Tables 2 and 3 show that the coumarin nucleus used in the invention, which corresponds to coumarin 102, has the best fluorescence, absorbance and chemiluminescence properties.

Table 4 gives the results obtained with respect to the chemiluminescence efficiency $R_C$ using TCPO and $H_2O_2$ as a function of the coumarin 102 concentration, as well as the Imax, Tmax and T½ values. These results show that the chemiluminescence efficiency increases with the coumarin 102 concentration.

Table 5 gives the variations of the chemiluminescence efficiency, Imax, Tmax and T½, as a function of the pH of the solution. The results obtained show that the chemiluminescence efficiency rises up to pH6 and then falls.

However, the Tmax and T½ values decrease when the pH increases beyond 5. The maximum intensity increases significantly with the pH.

TABLE 1

| Reagent | Detection Limit (fmole) | | Disadvantages |
|---|---|---|---|
| | Fluorescence | Chemiluminescence | |
| Luminarine-1 | 380 | TCPO: 2 DNPO: 1 | |
| Dansyl chloride | 100 | TCPO: 10 DNPO: 5 | Toxicity, inverted phase only |
| Orthophthaladehyde | 2100 | TCPO: 94 | Low sensitivity |
| Fluorescamine | 500 | TCPO: 25 | Restricted applications |
| Aminobutyl-ethyl isoluminol | — | 20 | Reaction time: 4H |
| Nitro benzoxadiazole chloride | 170 | TCPO: 19 | Low sensitivity with standard equipment |

TABLE 2

| | RF¹ | ε 365 nm | S 10³ |
|---|---|---|---|
| COUMARIN-102 | 0.57 | 23 100 | 36 |
| COUMARIN-1 | 0.55 | 38 000 | 57 |
| COUMARIN-311 | 0.52 | 26 900 | 40 |

RF = quantity efficiency of fluorescence.
ε = molecular extinction coefficient
S = fluorescence sensitivity

TABLE 3

| | DNPO | | TCPO | |
|---|---|---|---|---|
| | $R_C$ 10²E·mole⁻¹ | $R_E$ 10⁻² | $R_C$ 10²E·mole⁻¹ | $R_E$ 10² |
| COUMARIN-102 | 0.26 | 0.45 | 0.37 | 0.65 |
| COUMARIN-1 | 0.18 | 0.33 | 0.37 | 0.67 |
| COUMARIN-311 | 0.13 | 0.24 | 0.17 | 0.32 |

$R_c$ = quantity efficiency of chemiluminescence
$R_E$ = excitation efficiency
DNPO = bis-(2,4-dinitrophenyl)-oxalate
TCPO = bis-(2,4,6-trichlorophenyl)-oxalate

TABLE 4

| $(C_{102})$ E·mol⁻¹ | $R_C \times 10^4$ E·mol⁻¹ | Imax A.U. | Tmax min. | T½ min. |
|---|---|---|---|---|
| 1.4 × 10⁻³ | 12.0 | 301 | 0.2 | 0.10 |
| 1.4 × 10⁻⁶ | 4.14 | 75 | 0.2 | 0.15 |
| 1.4 × 10⁻⁷ | 2.31 | 31 | 0.2 | 0.12 |
| 1.4 × 10⁻⁸ | 0.40 | 3.2 | 0.2 | 0.10 |
| 1.4 × 10⁻⁹ | 0.20 | 0.3 | 0.2 | 0.08 |

TABLE 5

| pH | $R_C \times 10^4$ E·mol⁻¹ | Imax A.U. | Tmax min. | T½ min. |
|---|---|---|---|---|
| 4 | 1.52 | 24 | 0.8 | 5.0 |
| 5 | 1.58 | 17 | 1.0 | 6.0 |
| 6 | 2.34 | 25 | 0.8 | 5.6 |
| 7 | 2.23 | 110 | 0.4 | 1.8 |
| 8 | 1.60 | 245 | 0.2 | 0.4 |

We claim:

1. A derivative of tetrahydro-2,3,6,7,1H,5H,11H-(1)benzopyrano (6,7,8-ij)quinolizinone, characterized in that it complies with the formula:

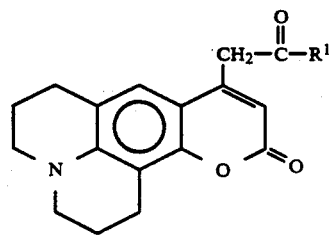

in which R¹ represents the radical of formula:

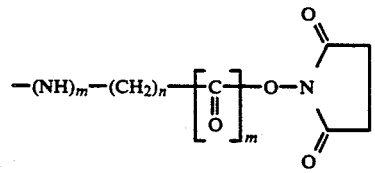

in which m is equal to 0 or to 1 and n is equal to 0 or is an integer from 1 to 12, provided that n is equal to 0 when m is equal to 0, or the radical of formula:

—NH—(CH₂)ₙ—NH₂ in which n has the meaning given hereinbefore.

2. A derivative according to claim 1, characterized in that R¹ represents the radical:

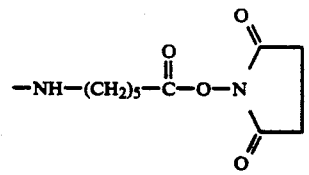

3. A derivative according to claim 1, characterized in that R¹ represents the radical:

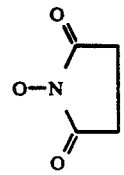

4. A derivative according to claim 1, characterized in that R¹ represents the radical —NH—NH₂.

5. A derivative according to claim 1, characterized in that R¹ represents the radical —NH—(CH₂)₄—NH₂.

6. A process for the preparation of a derivative of formula:

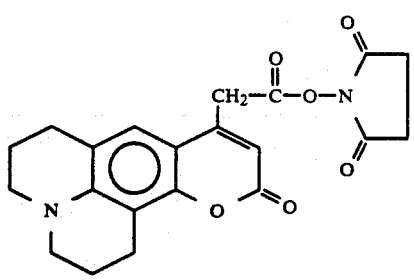

characterized in that it comprises the following successive stages:
1) reacting 8-hydroxyjulolidine of formula:

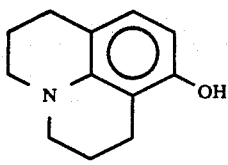

with an oxo-3-glutaric acid alkyl ester of formula:

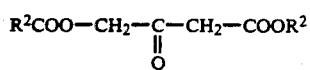

in which $R^2$ is an alkyl radical to form a compound of formula:

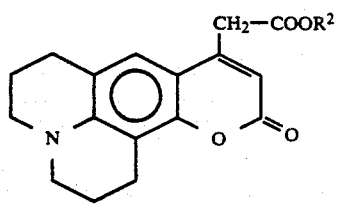

2) hydrolyzing the previously obtained alkyl ester of formula (VII) to obtain the acid of formula:

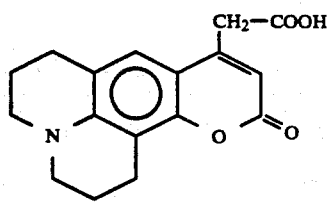

3) reacting the thus obtained acid of formula of (VIII) with dihydroxysuccinimide oxalate of formula:

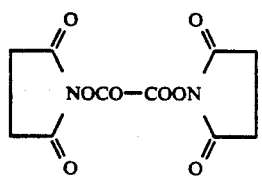

7. A process according to claim 6, characterized in that the oxo-3-glutaric acid alkyl ester is ethyl ester.

8. A process for the preparation of a derivative of tetrahydro-2,3,6,7,1H,5H,11H-(1)benzopyrano(6,7,8-ij)quinolizinone-11 according to formula:

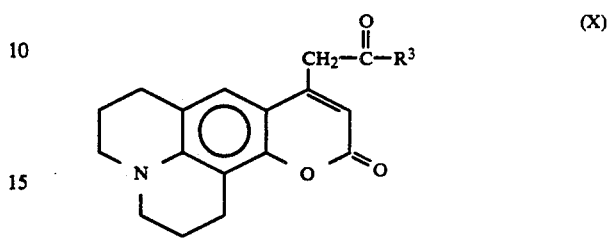

in which $R^3$ represents the radical of formula:

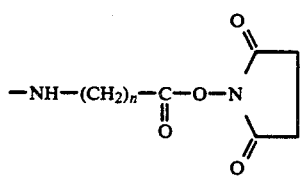

in which n is an integer from 1 to 12, characterized in that it comprises the following successive stages:
a) reacting the compound of formula:

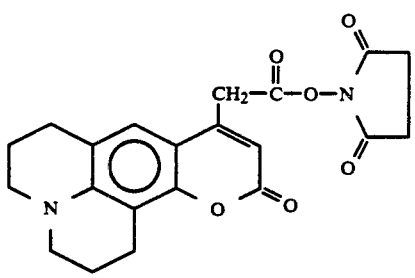

with an alkyl aminocarboxylate of formula:

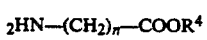

in which $R^4$ is an alkyl radical with 1 to 4 carbon atoms and n has the meaning given hereinbefore in order to form a compound of formula:

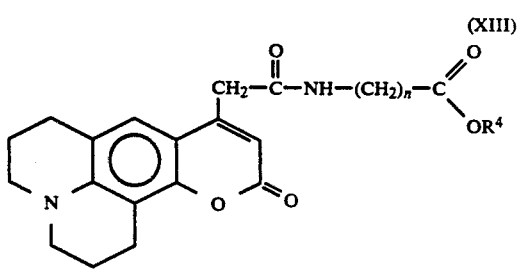

b) hydrolyzing the ester of formula (XIII) obtained to form the acid of formula:

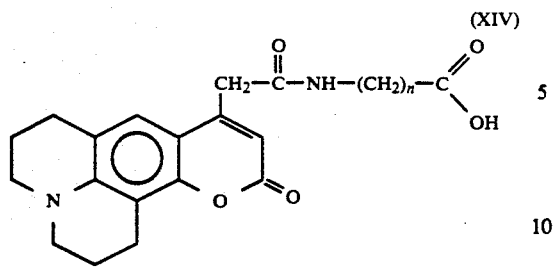

(XIV)

c) reacting the thus obtained acid of formula (XIV) with
1) dihydroxysuccinimide carbonate of formula:

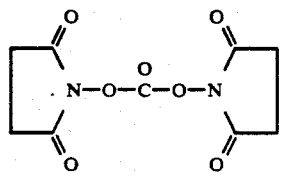

(XV)

2) dihydroxysuccinimide oxalate or
3) hydroxysuccinimide in the presence of dicyclohexyl carbodiimide.

9. A process for the preparation of a derivative of tetrahydro-2,3,6,7,1H,5H,11H-(1)benzopyrano(6,7,8ij)-quinolizinone-11 according to formula:

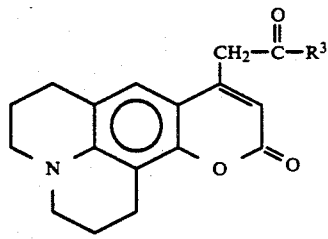

(X)

in which $R^3$ represents the radical of formula:

—NH—$(CH_2)_n$—$NH_2$ in which n is an integer from 1 to 12, characterized in that it comprises reacting the compound of formula:

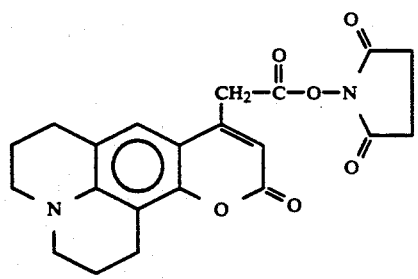

(II)

with a diaminoalkane of formula:

$_2HN$—$(CH_2)_n$—$NH_2$ in which n has the meaning given hereinbefore.

10. A process for the preparation of a derivative of tetrahydro-2,3,6,7,1H,5H,11H-(1)benzopyrano(6,7,8-ij)quinolizinone-11 according to formula:

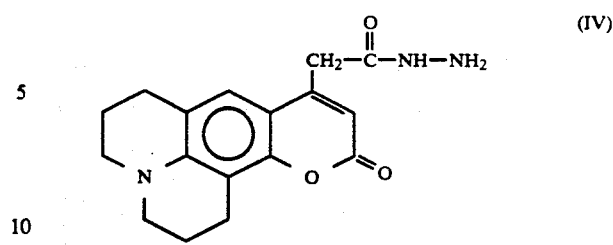

(IV)

characterized in that it comprises the following successive stages:
1) reacting the 8-hydroxyjulolidine of formula:

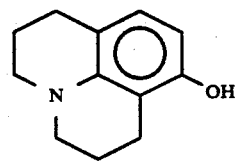

(VI)

with an oxo-3-glutaric acid alkyl ester of formula:

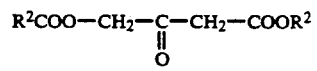

$R^2COO$—$CH_2$—$\underset{\underset{O}{\|}}{C}$—$CH_2$—$COOR^2$ in which $R^2$ is an alkyl radical for forming a compound of formula:

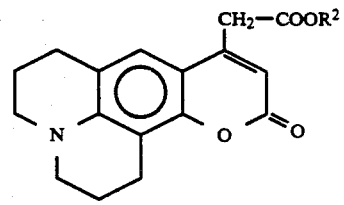

(VII)

2) reacting the alkyl ester of formula (VII) obtained in this way with hydrazine hydrate $_2HN$-$NH_2$, $H_2O$.

11. A process according to claim 10, characterized in that the oxo-3-glutaric acid alkyl ester is ethyl ester.

12. A process according to claim 8, characterized in that $R^3$ represents:

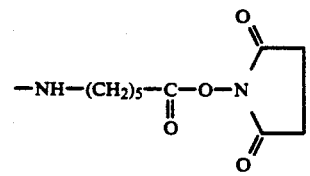

13. A process according to claim 9, characterized in that $R^3$ represents:

—NH—$(CH_2)_4$—$NH_2$

14. A process for the detection of a compound having a primary or secondary amine function by liquid chromatography, characterized in that it consists of reacting the compound to be detected with a derivative complying with the formula:

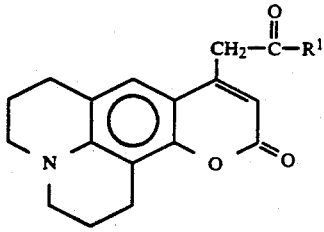

in which R¹ represents the radical of formula:

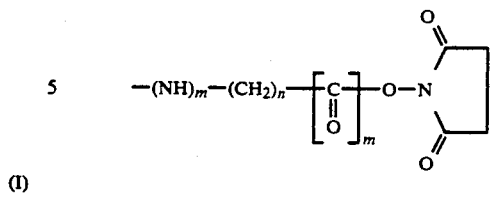

(I)

in which m=0 or 1 and n=0 or an integer from 1 to 12, provided that n=0 when m=0, to form a derivative of the compound to be detected, then carrying out a separation of said derivative by liquid chromatography and then detecting the derivative by absorptiometry, fluorimetry or chemiluminescence.

15. A process according to claim 14, characterized in that detection takes place by chemiluminescence using an oxalic ester or hydrogen peroxide.

16. A process according to claim 15, characterized in that the oxalic ester is bis-(2,4,6-trichlorophenyl)-oxalate or bis-(2,4-dinitrophenyl)-oxalate.

* * * * *